United States Patent
Emenike et al.

(10) Patent No.: US 7,145,053 B1
(45) Date of Patent: Dec. 5, 2006

(54) MOISTURE INDICATOR FOR A DIAPER

(76) Inventors: Christian Emenike, 2061 Raymond Ave., Bronx, NY (US) 10462; Chinwe Chris-Emenike Emenike, 2061 Raymond Ave., Bronx, NY (US) 10462

( * ) Notice: Subject to any disclaimer, the term of this patent is extended or adjusted under 35 U.S.C. 154(b) by 123 days.

(21) Appl. No.: 10/992,507

(22) Filed: Nov. 18, 2004

(51) Int. Cl.
- A61F 13/15 (2006.01)
- G08G 23/00 (2006.01)
- G08B 21/00 (2006.01)
- H01H 29/00 (2006.01)

(52) U.S. Cl. ............. 604/361; 604/362; 340/604; 340/605; 340/573.5; 200/61.04; 200/61.05; 200/61.02

(58) Field of Classification Search .......... 604/361, 604/362; 340/604, 605; 200/61.04, 61.05
See application file for complete search history.

(56) References Cited

U.S. PATENT DOCUMENTS

| 5,790,036 A | 8/1998 | Fisher | 340/605 |
| 5,868,723 A | 2/1999 | Al-Sabah | 604/361 |
| 6,246,330 B1 | 6/2001 | Nielsen | 340/604 |

*Primary Examiner*—Jacqueline F. Stephens
(74) *Attorney, Agent, or Firm*—Goldstein Law Offices PC.

(57) ABSTRACT

A battery operated moisture indicator for selective attachment to an existing diaper worn by a baby, having an audible alarm and having a liquid crystal display bulb, for providing an audible alert and a visual alert, respectively, when the diaper has been wet by the baby. The circuit includes a mechanism for selectively activating the alarm and the liquid crystal display bulb when an aqueous electrolyte-containing solution has wetted the diaper. The moisture indicator is provided with a diaphanous sac having a clip for selectively attaching the moisture indicator to the external surface of the front of an existing diaper, thereby providing a moisture indicator that is comfortable for a baby to wear.

5 Claims, 2 Drawing Sheets

MOISTURE INDICATOR FOR A DIAPER

BACKGROUND OF THE INVENTION

1. Field of the Invention

The invention generally relates to a moisture indicating device, and in particular relates to a battery operated moisture indicator for selective attachment to an existing diaper worn by a baby, having an audible alarm and having a liquid crystal display bulb, for providing an audible alert and a visual alert, respectively, when the diaper has been soiled by the baby.

2. Description of the Related Art

Disposable diapers are used by parents worldwide for containment of a baby's excreted waste prior to changing the diapers, and for keeping the baby's bottom clean and dry so as to prevent diaper rash. Although diapers have continually been improved over the years, use of a diaper still has a notable disadvantage. In particular, diapers must be changed as often as a baby excretes into the diaper. However, a parent or a caregiver cannot always visually determine upon casual inspection whether the baby has soiled the diaper with waste, particularly when the volume of excreted waste is relatively small. Consequently, a parent must ascertain whether the diaper is soiled by actually feeling the fabric of the diaper with the fingers, or by opening up the diaper by detaching the adhesive or Velcro tabs used to secure the diaper in place. Feeling a diaper for wetness is an unpleasant and unsanitary task. Moreover, repeatedly opening and closing the tabs of a diaper may fray the tabs, and thereby prevent the diaper from closing properly around the baby. Accordingly, there is a need for a moisture indicator for selective attachment to an existing diaper worn by a baby, having an audible alarm and having a liquid crystal display bulb, for providing an audible alert and a visual alert, respectively, when the diaper has been soiled by the baby, so that a parent or caretaker does not have to feel the fabric of the diaper for wetness with the fingers, or open up the diaper, in order to determine whether the baby has soiled the diaper with waste.

A variety of moisture sensing materials and systems, and methods for use thereof, have been devised. For example, U.S. Pat. No. 5,790,036 to Fisher appears to show a sensor for detecting fluids such as urine, for use in conjunction with an absorbent device such as a diaper, and capable of selectively vibrating and producing sound, light, or a radio signal in order to provide an alert. Additionally, U.S. Pat. No. 6,246,330 to Nielsen appears to show a monitoring system for a diaper which visually and audibly indicates the condition of the diaper. Furthermore, U.S. Pat. No. 5,868,723 to Al-Sabah appears to show a moisture sensor capable of audibly indicating whether a garment such as a diaper has been wet.

While these devices may be suitable for the particular purpose employed, or for general use, they would not be as suitable for the purposes of the present invention as disclosed hereafter.

SUMMARY OF THE INVENTION

It is an object of the invention to provide a moisture indicator for an existing diaper that emits an audible alert and a visual alert when the baby has soiled the diaper. Accordingly, the moisture indicator has an audible alarm and has a liquid crystal display bulb. When the baby has soiled the diaper, the audible alarm and the liquid crystal display bulb emit an audible alert and a visual alert, respectively, and thereby indicate that the baby has soiled the diaper.

It is another object of the invention to provide a moisture indicator that reduces the occurrence of diaper rash on a baby. Accordingly, because the moisture indicator emits an audible alert and a visual alert when the baby has soiled the diaper, a parent is alerted to change the diaper almost immediately after it has been soiled, thereby reducing the occurrence of diaper rash on the baby.

It is yet another object of the invention to provide a moisture indicator that saves the parent a great deal of time by obviating the need for the parent to continually check the status of the diaper by feeling the diaper with the fingers or by opening the diaper. Accordingly, because the moisture indicator emits an audible alert and a visual alert when the baby has soiled the diaper, the parent can readily determine whether the diaper has been soiled without having to continually check the status of the diaper by feeling the diaper with the fingers or by opening the diaper, and thereby saves the parent a great deal of time.

It is still another object of the invention to provide a moisture indicator that is comfortable for a baby to wear. Accordingly, the moisture indicator is compact in size and lightweight, and is provided with a diaphanous sac having a clip for selectively attaching the moisture indicator to the external surface of the front of an existing diaper, thereby providing a moisture indicator that is comfortable for a baby to wear.

Further objects of the invention will become apparent in the detailed description of the invention that follows.

The invention is a battery operated moisture indicator for selective attachment to an existing diaper worn by a baby, having an audible alarm and having a liquid crystal display bulb, for providing an audible alert and a visual alert, respectively, when the diaper has been wet by the baby. The circuit includes a mechanism for selectively activating the alarm and the liquid crystal display bulb when an aqueous electrolyte-containing solution has wetted the diaper. The moisture indicator is provided with a diaphanous sac having a clip for selectively attaching the moisture indicator to the external surface of the front of an existing diaper, thereby providing a moisture indicator that is comfortable for a baby to wear.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
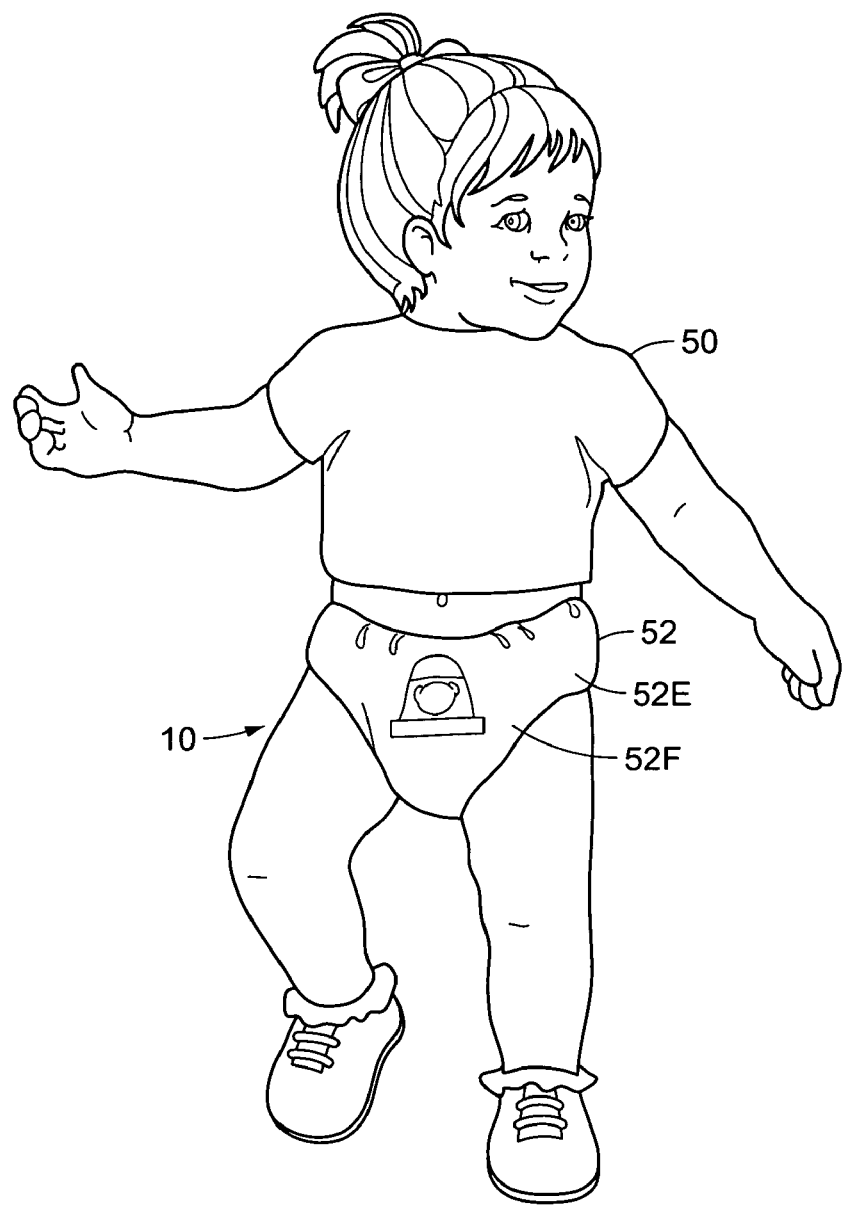
FIG. 1 is a perspective view of a baby wearing a diaper to which a moisture indicator has been selectively appended.

FIG. 1 illustrates a moisture indicator 10 after it has been selectively appended to an external surface 52E of the front 52F of an existing diaper 52 that is being worn by a baby 50. The moisture indicator 10 emits an audible alert and a visual alert when the baby 50 has soiled the diaper 52 by excreting waste, including urine and feces, into the diaper 52.

Figure 2:
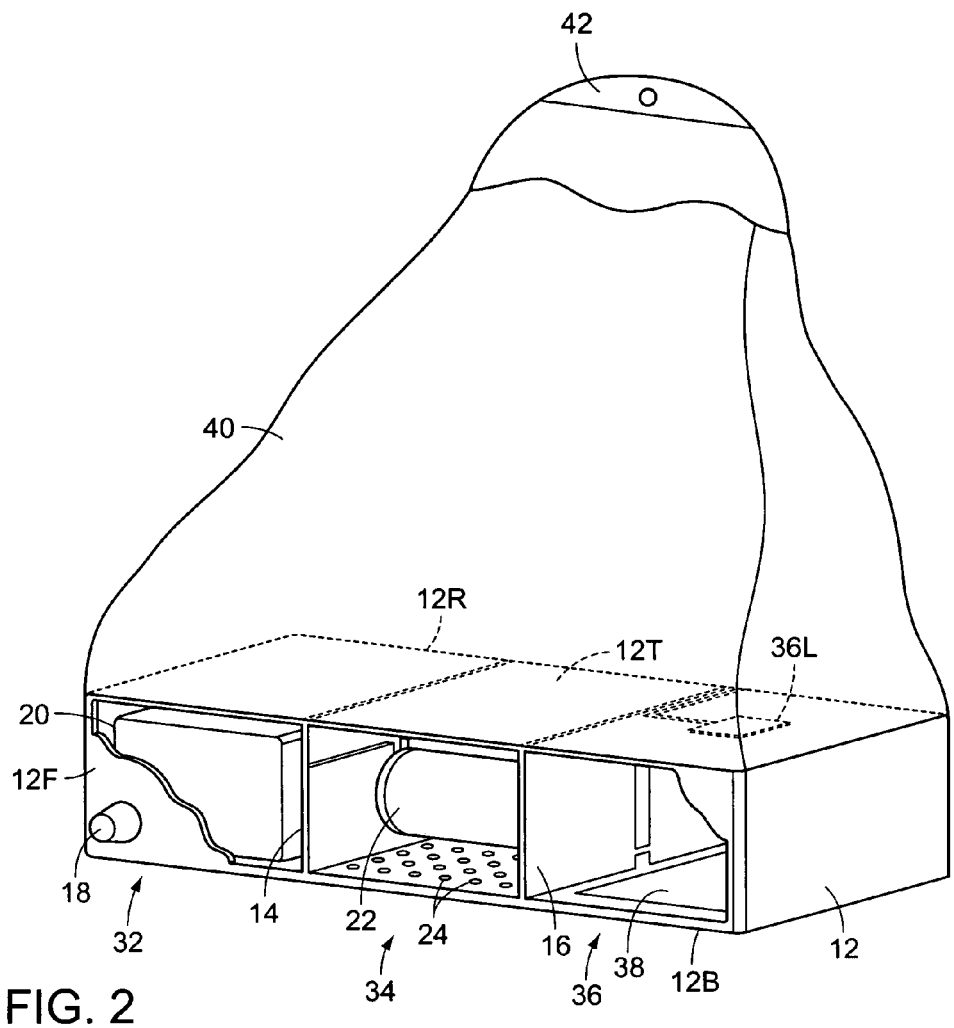
FIG. 2 is a perspective view of the moisture indicator, wherein a portion of a sac has been broken away in order to reveal a housing contained therein, and wherein portions of the housing have been broken away to reveal the three chambers contained therein.

FIG. 2 illustrates an enlarged view of the moisture indicator 10, comprising an electrical circuit which includes an audible alarm 20 which selectively emits an audible alert upon activation, and a liquid crystal display bulb 22 which selectively emits a visual alert upon activation. The moisture indicator 10 has a battery compartment 38 for housing a battery for selectively powering the audible alarm 20 and the liquid crystal display bulb 22. The circuit has an open position and a closed position, and has an ON/OFF switch 18 for selectively converting the circuit from the open position to the closed position. The ON/OFF switch 18 has an "on" position and an "off" position. The parent turns the switch 18 to the "off" position to selectively deactivate the alarm 20 and the liquid crystal display bulb 22. The circuit includes a mechanism 60 for selectively activating the alarm 20 and the liquid crystal display bulb 22 when the diaper 52 has been wetted with urine.

Figure 3:
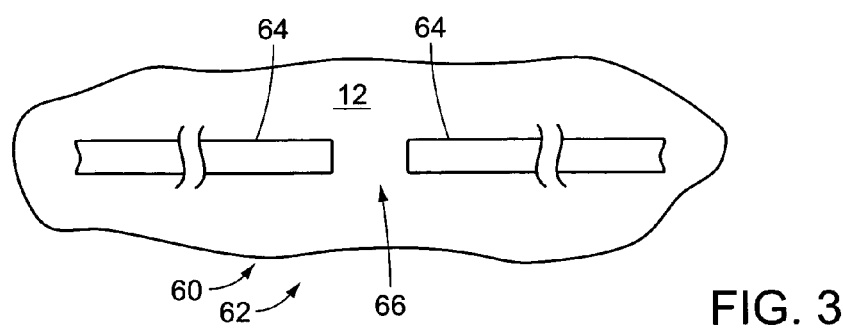
FIG. 3 is a schematic diagram of a mechanism for activating the alarm.

FIG. 3 depicts schematically one way in which such a mechanism 60 might operate. The mechanism 60 comprises a gap portion 62 within the electrical circuit, said gap portion 62 comprising at least two electrically conductive portions 64 separated from each other by a small gap 66. The gap 66 selectively opens and closes the circuit. In particular, when the ON/OFF switch 18 is in the "on" position, and when an aqueous solution containing electrolytes bridges the gap 66 between the separated electrically conductive portions 64, the circuit is closed, and the alarm 20 and the liquid crystal display bulb 22 are selectively activated.

The audible alarm 20, the liquid crystal display bulb 22, and the battery compartment 38 are contained within a three-chambered rectangular housing 12 having a front surface 12F, a rear surface 12R, a top surface 12T, and a bottom surface 12B. The housing 12 contains a first inner wall 14 and a spatially separated second inner wall 16, which, in conjunction with the front surface 12F, the rear surface 12R, the top surface 12T, and the bottom surface 12B, define three spatially separated chambers positioned in a side-by-side manner. These chambers include an alarm chamber 32 for housing the audible alarm 20, a light bulb chamber 34 for housing the liquid crystal display bulb 22, and a battery compartment chamber 36 which encloses the battery compartment 38. The ON/OFF switch 18 extends from the front surface 12F of the alarm chamber 32. The bottom surface 12B of the light bulb chamber 34 has a plurality of perforations 24 extending fully therethrough, through which light is emitted when the liquid crystal display bulb 22 is selectively activated. The top surface 12T of the battery compartment chamber 36 has a lid 36L which allows selective access to the battery contained within the battery compartment 38. The housing 12 is suspended within a diaphanous cellophane sac 40 having a top 40T and a bottom 40B. The diaphanous sac 40 allows the housing 12 to be suspended comfortably against the external surface 52E of the front 52F of the diaper 52 that is being worn by the baby 50. The top 40T of the sac 40 has a clip 42 attached thereunto, said clip 42 for selectively attaching the moisture indicator 10 to the external surface 52E of the front 52F of the diaper 52. A variety of well-known attachment methods including differently configured clips, Velcro strips, and detachable buckle assemblies may alternately be used for selectively securing the moisture indicator 10 to the front 52F of the diaper 52. The electrically conductive portions 64 of the gap portion 62 are located upon a surface of the housing 12 which contacts the diaper 52 after the moisture indicator 10 has been appended thereunto with the clip 42.

The moisture indicator 10 is preferably approximately 5 centimeters in length, 2 centimeters in width, and 2 centimeters in depth, so that it is compact and will not be uncomfortable for the baby 50 to wear.

In use, a parent dresses the child in an existing diaper 52, and appends the moisture indicator 10 to the external surface 52E of the front 52F of the diaper 52 with the clip 42. The baby 50 activates the mechanism 60 by wetting the diaper 52 with excreted waste. The electrolyte-containing liquid waste travels through the diaper 52 by capillary action, and bridges the gap 66 between the electrically conductive portions 64, and thereby causes the audible alarm 20 and the liquid crystal display bulb 22 to emit an audible alert and a visual alert, respectively, and thereby indicate that the baby 50 has soiled the diaper 52. The parent turns the ON/OFF switch 18 to the off position to deactivate the audible alarm 20 and the liquid crystal display bulb 22. The parent detaches the moisture indicator 10 from the diaper 52, removes the soiled diaper 52 from the baby 50, and replaces the soiled diaper 52 with a fresh diaper 52. The parent turns the ON/OFF switch 18 to the on position and appends the moisture indicator 10 to the external surface 52E of the front 52F of the fresh diaper 52 with the clip 42.

In conclusion, herein is presented a moisture indicator for selective attachment to an existing diaper worn by a baby, capable of providing an audible alert and a visual alert when the diaper has been wet by the baby. The invention is illustrated by example in the drawing figures, and throughout the written description. It should be understood that numerous variations are possible, while adhering to the inventive concept. Such variations are contemplated as being a part of the present invention.

What is claimed is:

1. A moisture indicator for selective attachment to an existing diaper worn by a baby, capable of providing an audible alert and a visual alert when the diaper has been wet by the baby, comprising:

an electrical circuit which includes an audible alarm which emits an audible alert upon selective activation, and a liquid crystal display bulb which emits an visual alert upon selective activation, said circuit having an open position and a closed position, and having an ON/OFF switch for selectively converting the circuit from the open position to the closed position and thereby selectively deactivating the alarm and the liquid crystal display bulb, wherein the circuit includes a mechanism for selectively activating the alarm and the liquid crystal display bulb when the diaper has been wetted by the baby;

a battery compartment for housing an existing battery for selectively powering the audible alarm and the liquid crystal display bulb;

a housing having a front surface, a rear surface, a top surface, a bottom surface, a first inner wall, and a spatially separated second inner wall, said surfaces and walls together defining three spatially separated chambers positioned in a side-by-side manner, said chambers including an alarm chamber for housing the audible alarm, a light bulb chamber for housing the liquid crystal display bulb, and a battery compartment chamber which encloses the battery compartment, said light bulb chamber having a plurality of perforations through which light is emitted when the liquid crystal display bulb is selectively activated; and a sac for suspending the housing comfortably against the external surface of the front of the diaper, said sac having a top and a bottom, wherein the top of the sac has a clip attached thereunto, said clip for selectively attaching the moisture indicator to the diaper.

2. The moisture indicator as recited in claim 1, wherein the sac is diaphanous.

3. The moisture indicator as recited in claim 2, wherein the sac is constructed from cellophane.

4. The moisture indicator as recited in claim 3, wherein the mechanism is located upon a surface of the housing which contacts the diaper after the moisture indicator has been appended thereunto with the clip.

5. A method of providing an audible alert and a visual alert to a parent when an existing diaper has been wet by a baby, said diaper having an external surface and a front, said method using a moisture indicator which is powered by an existing battery, said moisture indicator having an audible alarm which emits an audible alert upon selective activation, a liquid crystal display bulb which emits an visual alert upon selective activation, an ON/OFF switch, a mechanism for selectively activating the alarm and the liquid crystal display bulb when the diaper has been wet by the baby, a housing which defines three spatially separated chambers positioned in a side-by-side manner, said chambers including an alarm chamber for housing the audible alarm, a light bulb chamber for housing the liquid crystal display bulb, and a battery compartment chamber for housing the battery, said moisture indicator having a diaphanous sac in which the housing is suspended, said sac having a clip attached thereunto, said method comprising the steps of:

dressing the child in the diaper;

appending the diaphanous sac to the external surface of the front of the diaper with the clip;

activating the mechanism by the baby wetting the diaper, and thereby causing the audible alarm and the liquid crystal display bulb to emit an audible alert and a visual alert, respectively, thereby indicating that the baby has wet the diaper;

deactivating the audible alarm and the liquid crystal display bulb with the ON/OFF switch;

detaching the sac from the diaper by detaching the clip from the diaper;

removing the wet diaper from the baby and dressing the baby in a dry diaper; and appending the sac to the external surface of the front of the dry diaper with the clip.

* * * * *